US011717644B2

(12) United States Patent
Douglas et al.

(10) Patent No.: US 11,717,644 B2
(45) Date of Patent: *Aug. 8, 2023

(54) ROBOTICALLY AUGMENTED CATHETER MANIPULATION HANDLE

(71) Applicant: Nextern, Inc., White Bear Lake, MN (US)

(72) Inventors: Ryan Douglas, Stillwater, MN (US); Richard Farrell, Delwood, MN (US); Dennis Berke, River Falls, WI (US); Davis Flanagan, Saint Paul, MN (US); David Bontrager, Minneapolis, MN (US); Brian Loushine, Minnetonka, MN (US)

(73) Assignee: Nextern Innovation, LLC, White Bear Lake, MN (US)

( * ) Notice: Subject to any disclaimer, the term of this patent is extended or adjusted under 35 U.S.C. 154(b) by 536 days.

This patent is subject to a terminal disclaimer.

(21) Appl. No.: 16/861,633

(22) Filed: Apr. 29, 2020

(65) Prior Publication Data

US 2020/0254219 A1    Aug. 13, 2020

Related U.S. Application Data

(63) Continuation of application No. 15/425,982, filed on Feb. 6, 2017, now Pat. No. 10,675,442.

(Continued)

(51) Int. Cl.
*A61M 25/01* (2006.01)

(52) U.S. Cl.
CPC .... *A61M 25/0136* (2013.01); *A61M 25/0113* (2013.01); *A61M 2025/0166* (2013.01);
(Continued)

(58) Field of Classification Search
CPC .......... A61M 25/0113; A61M 25/0136; A61M 2025/0166; A61B 34/70; A61B 2034/301
See application file for complete search history.

(56) References Cited

U.S. PATENT DOCUMENTS 5,626,595 A *  5/1997  Sklar .............. A61B 17/320016
                                              606/180
5,643,255 A    7/1997  Organ
               (Continued)

FOREIGN PATENT DOCUMENTS

CN    101918073 A    12/2010
CN    103379853 A    10/2013
               (Continued)

OTHER PUBLICATIONS

Taylor, R. and Stoianovici, D., Medical Robotics in Computer-Integrated Surgery, IEEE Transactions on Robotics and Automation, Oct. 2003, p. 765-781, vol. 19 No. 5, IEEE, NY.
(Continued)

*Primary Examiner* — Laura A Bouchelle
(74) *Attorney, Agent, or Firm* — Craige Thompson; Thompson Patent Law; Timothy D. Snowden (57) ABSTRACT

Apparatus and associated methods relate to a catheter manipulation handle with user interface controls for steering a catheter in situ while providing an augmented (e.g., motorized, powered and tunable precision steering, and perforation safeguards) control and feedback user experience. In an illustrative example, the catheter manipulation handle may provide motor assisted operation to automatically rotate and/or deflect a distal tip of the catheter to steer and guide the distal tip to a target location in the patient's vasculature system. The augmented feedback may include, for example, haptic feedback via the handle. Haptic, audible, and/or visual feedback via the handle may indicate, for example, proximity or engagement of the distal tip with
(Continued)

sensitive tissue. In some examples, the handle's augmented operation may advantageously amplify feedback signals to enhance the user's perception of the patient's safety with respect to the safe passage of the distal tip through the patient's vasculature.

20 Claims, 7 Drawing Sheets

Related U.S. Application Data (60) Provisional application No. 62/292,699, filed on Feb. 8, 2016.

(52) U.S. Cl.
CPC ............... *A61M 2205/332* (2013.01); *A61M 2205/3331* (2013.01); *A61M 2205/3379* (2013.01)

(56) References Cited

U.S. PATENT DOCUMENTS

| | | | |
|---|---|---|---|
| 5,891,088 | A | 4/1999 | Thompson et al. |
| 6,823,217 | B2 | 11/2004 | Rutten et al. |
| 6,997,870 | B2 | 2/2006 | Couvillon, Jr. |
| 7,931,616 | B2 | 4/2011 | Selkee |
| 8,190,238 | B2 | 5/2012 | Moll et al. |
| 8,202,244 | B2* | 6/2012 | Cohen ............ A61M 25/0105 604/95.01 |
| 8,900,228 | B2 | 12/2014 | Grunewald et al. |
| 8,956,304 | B2 | 2/2015 | Schecter |
| 9,220,433 | B2 | 12/2015 | Ditter et al. |
| 9,414,878 | B1 | 8/2016 | Wu et al. |
| 10,675,442 | B2* | 6/2020 | Douglas ........... A61M 25/0147 |
| 2007/0103437 | A1 | 5/2007 | Rosenberg |
| 2008/0214896 | A1 | 9/2008 | Krupa et al. |
| 2008/0228104 | A1 | 9/2008 | Uber et al. |
| 2008/0243064 | A1 | 10/2008 | Stabler et al. |
| 2008/0255540 | A1 | 10/2008 | Selkee |
| 2011/0060346 | A1 | 3/2011 | Jensen et al. |
| 2012/0071752 | A1 | 3/2012 | Sewell et al. |
| 2012/0143088 | A1 | 6/2012 | Schultz |
| 2012/0179070 | A1 | 7/2012 | Pommer et al. |
| 2012/0184955 | A1 | 7/2012 | Pivotto et al. |
| 2012/0203142 | A1 | 8/2012 | Bedell |
| 2013/0321262 | A1 | 12/2013 | Schecter |
| 2014/0018732 | A1 | 1/2014 | Bagaoisan et al. |
| 2014/0107427 | A1 | 4/2014 | Chow et al. |
| 2014/0276934 | A1 | 9/2014 | Balaji et al. |
| 2015/0073340 | A1 | 3/2015 | Pacheco et al. |
| 2015/0153842 | A1 | 6/2015 | Obermeyer et al. |
| 2015/0216553 | A1 | 8/2015 | Kessler et al. |
| 2016/0000499 | A1 | 1/2016 | Lennox et al. |
| 2016/0278841 | A1 | 9/2016 | Panescu et al. |

FOREIGN PATENT DOCUMENTS

| | | |
|---|---|---|
| WO | 03088204 A1 | 10/2003 |
| WO | 2011109283 A1 | 9/2011 |

OTHER PUBLICATIONS

Poty, H., et al., Robotic atrial fibrillation ablation . . . , Oct. 1, 2014, [online], [retrieved Jan. 27, 2017].<URL: https://www.youtube.com/watch?v=xPXHHCJ6icQ#t=261.7068103>.

Hansen Medical, Inc., Magellen Live Patient Case at TCT, Nov. 29, 2013 [online], [retrieved Jan. 27, 2017], <URL: https://www.youtube.com/watch?v=vzf9AFndpcw>.

Okamura, A., Haptic Feedback in Robot-Assisted Minimally Invasive Surgery, Current Opinion in Urology, Jan. 2009, p. 102-107, vol. 19(1), Wolters Kluwer Health, Phil., PA.

Filgueiras-Rama, D. and Merino, J., The Future of Pulmonary Vein Isolation, Arrythmia Electrophysiology Rev., Apr. 2013, p. 59-64, vol. 2(1), Radcliffe Card., UK.

Adib et al., "Direct-write 3D printing and characterization of a GelMA-based biomaterial for intracorporeal tissue engineering," Biofabrication, vol. 12, No. 4, Art. No. 4, Jul. 2020, <doi: 10.1088/1758-5090/ab97a1>.

* cited by examiner

FIG.7B

ROBOTICALLY AUGMENTED CATHETER MANIPULATION HANDLE

CROSS-REFERENCE TO RELATED APPLICATIONS

This application is a Continuation and claims the benefit of U.S. application Ser. No. 15/425,982 titled "Robotically Augmented Catheter Manipulation Handle," filed by Douglas, et al. on Feb. 6, 2017, which claims the benefit of U.S. Provisional Application Ser. No. 62/292,699 titled "Robotically Assisted Steerable Catheter," filed by Douglas, et al. on Feb. 8, 2016.

This application incorporates the entire contents of the foregoing application(s) herein by reference.

TECHNICAL FIELD

Various embodiments relate generally to catheter control mechanisms that augment catheter steering directly controlled by a medical professional.

BACKGROUND

Medical teams have available a wide variety of catheters, to enable provision of the right products for their patients' unique medical needs. For decades, with the help of catheters, medical teams have been able to drain fluids from body cavities, administer medications intravenously, perform surgical procedures and administer anesthetics, for example. As technology progressed, medical instrument designers provided modern medicine teams with guiding catheters and sheaths. Guiding catheters and sheaths are frequently used in many medical procedures due to their minimally invasive nature. For example, patients undergoing cardiac or other vascular procedures with guiding catheters and sheaths receive a minimally-sized surgically-placed lumen (opening) to the skin.

Guiding catheters and sheaths, otherwise named "steerable" catheters and sheaths, employ control wires that pass from the catheter interface through the catheter shaft and terminate at the catheter shaft tip. Tension applied to any of the control wires causes the catheter tip to deflect, giving control of orientation to the catheter tip, for example giving orientation control of the imaging angle of a tip mounted ultrasound transducer. This technology has made more advanced procedures possible using catheter-mounted instruments, benefiting patients with minimally invasive procedures, by entering a patient's body percutaneously or via natural orifices. Further descriptions that reference guided catheters may also apply to guided sheaths.

SUMMARY

Apparatus and associated methods relate to a catheter manipulation handle with user interface controls for steering a catheter in situ while providing an augmented (e.g., motorized, powered and tunable precision steering, and perforation safeguards) control and feedback user experience. In an illustrative example, the catheter manipulation handle may provide motor assisted operation to automatically rotate and/or deflect a distal tip of the catheter to steer and guide the distal tip to a target location in the patient's vasculature system. The augmented feedback may include, for example, haptic feedback via the handle. Haptic, audible, and/or visual feedback via the handle may indicate, for example, proximity or engagement of the distal tip with sensitive tissue. In some examples, the handle's augmented operation may advantageously amplify feedback signals to enhance the user's perception of the patient's safety with respect to the safe passage of the distal tip through the patient's vasculature.

Various embodiments may achieve one or more advantages. For example, some embodiments may employ an integrated active display to present images with a customizable user interface, which may advantageously provide control of a catheter manipulation handle (CMH) with finger sliding motions, and providing a modern look.

In some embodiments, the CMH may determine the best control pattern based on preferences input by the user, and may advantageously allow a user to recall from CMH memory, common, particularly challenging or lengthy catheter move sequences from the CMH memory.

In some embodiments, the user may be in direct contact with the CMH, holding the CMH in the hand, such that the forces on the catheter from the catheter tip hitting a vessel wall, for example, may be felt directly by the user, which may advantageously provide a natural haptic feedback. In some examples the various forces on the guide catheter are minute and may not be substantially felt by the user holding the CMH. In some embodiments, haptic feedback may be artificially induced into the handle, for instance with vibratory, audible, and/or visual feedback, which may advantageously provide a heightened sensor feedback experience for the user. In various implementations, a surgeon may prefer to directly manipulate the patient-catheter interaction by receiving augmented feedback signals supplied via the handle gripped by the surgeon.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 1:
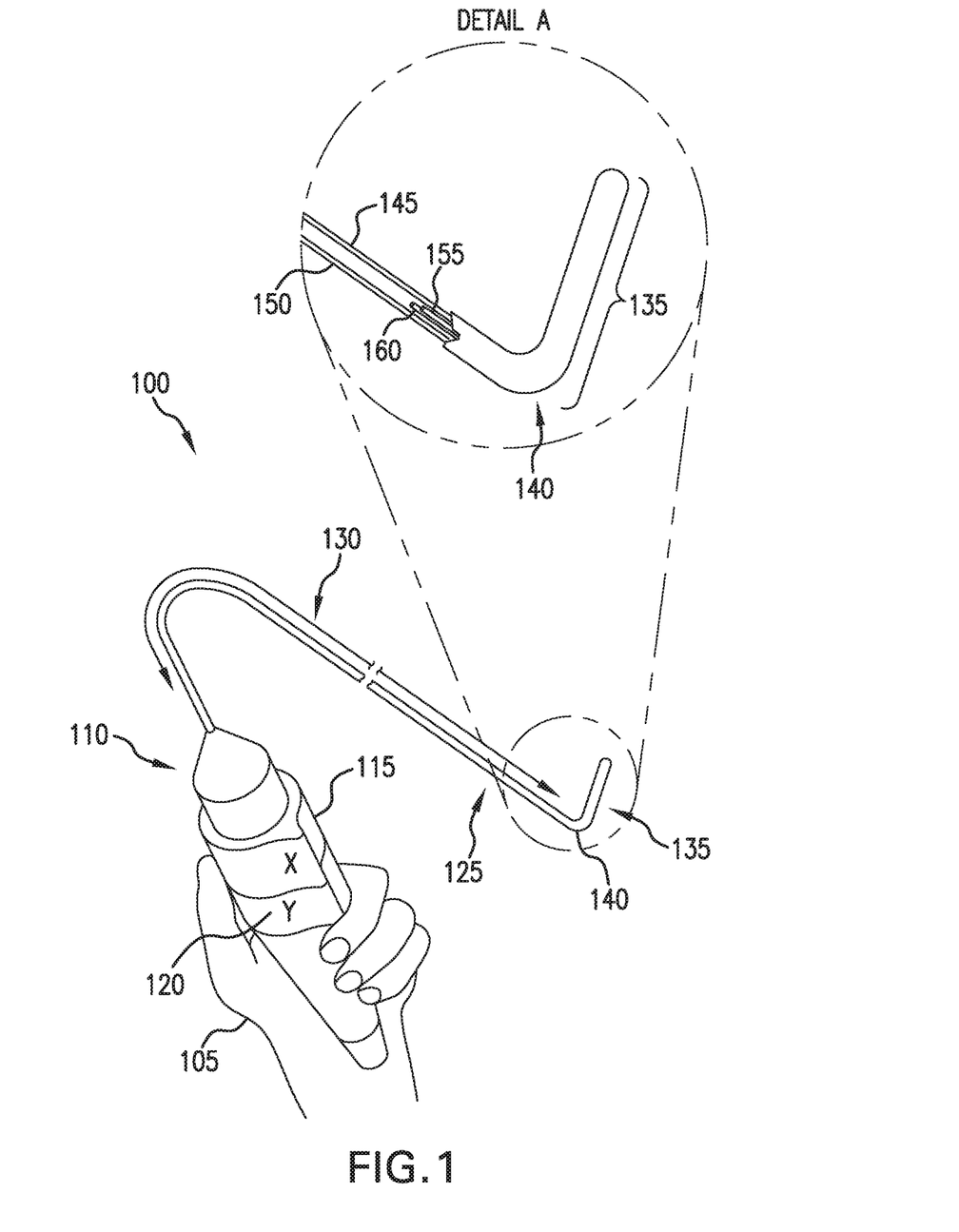
FIG. 1 depicts a perspective view of an exemplary catheter manipulation handle (CMH) in a user's hand illustrating operation.
Figure 2:
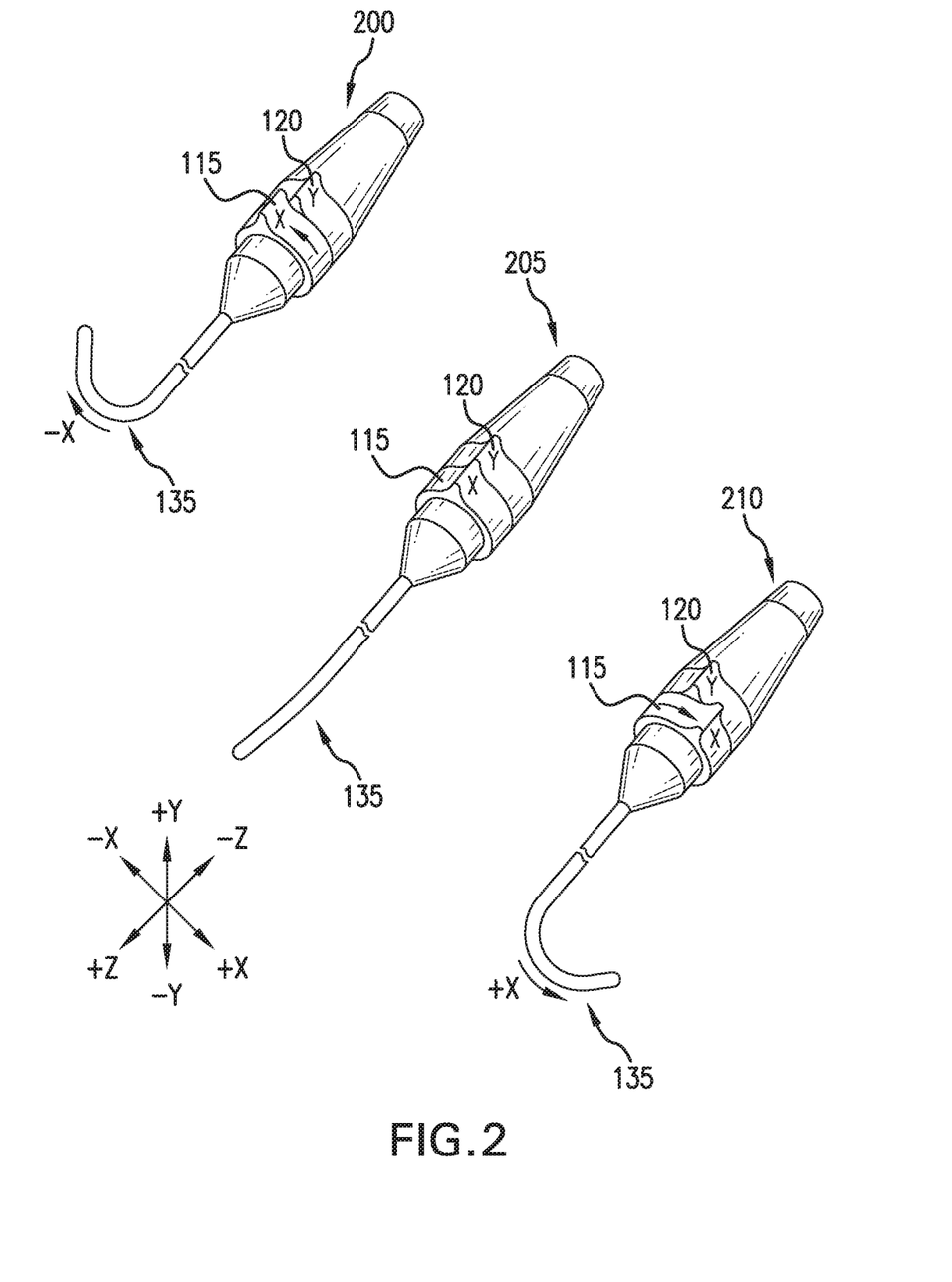
FIG. 2 depicts a perspective view of an exemplary CMH, illustrating specific functionality.

To aid understanding, this document is organized as follows. First, an exemplary catheter manipulation handle (CMH) is briefly introduced with reference to FIGS. 1-2 illustrating the CMH operation. Second, with reference to FIG. 3, discussion turns to exemplary embodiments that illustrates CMH components, specifically an exemplary enclosure and components attached to an outer enclosure. Third, with reference to FIG. 4, a functional block diagram is presented. Finally, with reference to FIGS. 5-7, additional embodiments are presented to illustrate other exemplary configurations.

FIG. 1 depicts a perspective view of an exemplary catheter manipulation handle (CMH) in a user's hand illustrating operation. A guide catheter in a pre-insertion use case 100, is held by a doctor 105. The doctor 105 holds a CMH 110, testing its operation. The CMH 110 contains an X deflection collar 115 and a Y deflection collar 120. The X deflection collar 115 and the Y deflection collar 120 may employ a detent position in the center of their travel. The doctor may rotate the X deflection collar 115 and the Y deflection collar 120 independently to control a catheter 125 shape. The catheter 125 is made up of 2 sections: the catheter proximal section 130 and the catheter distal end 135. Between the catheter proximal section 130 and the catheter distal end 135, in this embodiment, lies the distal bend 140. The doctor 105 may manipulate the shape of the distal bend 140 by employment of the X deflection collar 115 and the Y deflection collar 120, advantageously direct the catheter distal end 135. During a medical procedure, the catheter 125 may be directed into a lumen on a patient and advanced into the patient's vascular system. As the catheter 125 is advanced, the doctor 105 may direct the catheter distal end 135 by rotating the X deflection collar 115 and the Y deflection collar 120 to steer the catheter into the desired vascular path.

In detail A, the catheter distal end 135 has been cut away to show the control wires. The X deflection collar 115 controls a first X deflection steering wire 145 and a second X deflection steering wire 150, such that pulling on the first X deflection steering wire 145 and releasing the second X deflection steering wire 150, may deflect the catheter distal end 135 in one direction, for example to the left, and such that pulling on the second X deflection steering wire 150 and releasing the first X deflection steering wire 145, may deflect the catheter distal end 135 in the opposite direction, for example to the right. (See FIG. 2).

The Y deflection collar 120 controls a first Y deflection steering wire 155 and a second Y deflection steering wire 160, such that pulling on the first Y deflection steering wire 155 and releasing the second Y deflection steering wire 160, may deflect the catheter distal end 135 in one direction, for example upward, and such that pulling on the second Y deflection steering wire 160 and releasing the first Y deflection steering wire 155, may deflect the catheter distal end 135 in the opposite direction, for example downward.

In some embodiments, the X and Y steering functionality may be accomplished with fewer control wires, for example 1 wire for the X deflections and 1 wire for the Y deflections. In some embodiments, the X and Y steering functionality may be accomplished with more control wires.

FIG. 2 depicts a perspective view of an exemplary CMH, illustrating specific functionality. The CMH is depicted in 3 specific catheter distal end 135 deflection functions: deflection in the −x direction 200, no deflection 205, and deflection in the +x direction 210. Deflection in the −x direction 200, is accomplished by moving the X deflection collar 115 in the counter clockwise (CCW) direction as viewed from the catheter side of the CMH. The Y deflection collar 120 moves the catheter in the Y direction, and is not used in this functional use case. No deflection 205, is accomplished by leaving the X deflection collar 115, and the Y deflection collar 120 in their detent positions. Deflection in the +x direction 210, is accomplished by moving the X deflection collar 115 in the clockwise (CW) direction as viewed from the catheter side of the CMH. The Y deflection collar 120 moves the catheter in the Y direction, and is not used in this functional use case.

Figure 3:
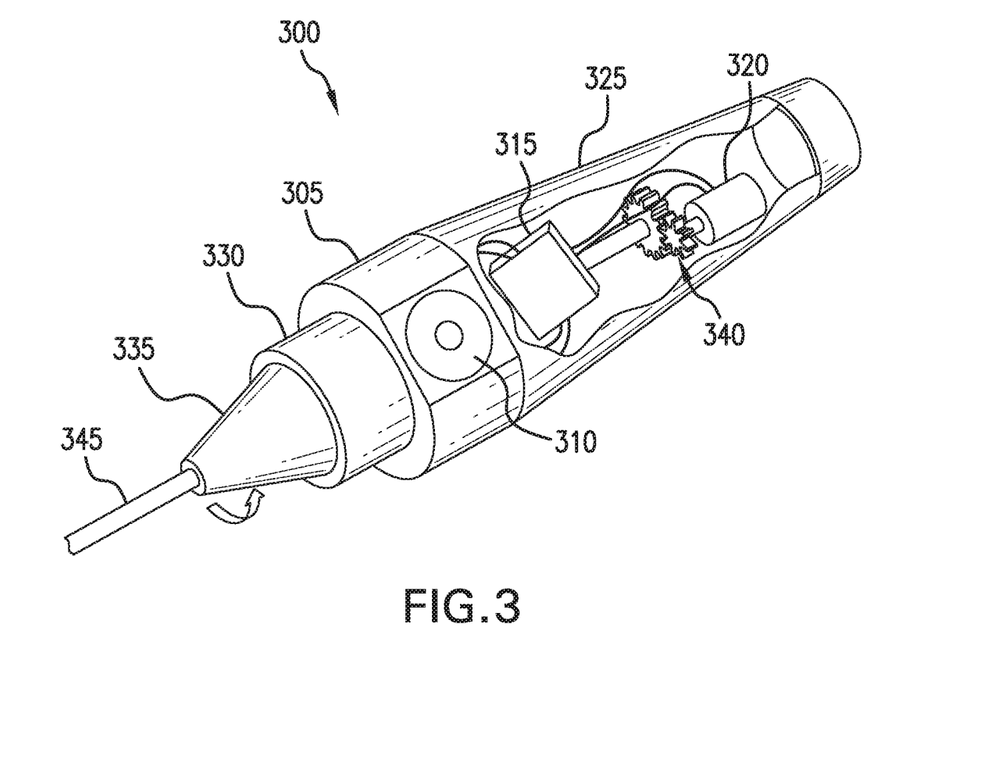
FIG. 3 depicts a perspective view of an exemplary CMH.

FIG. 3 depicts a perspective view of an exemplary CMH. The exemplary CMH 300 contains a collar 305. The collar 305 attaches to a capacitive touch wheel 310. The capacitive touch wheel 310 is wired to a control board 315 via a first wire harness for example. The control board 315 is also wired to the electromechanical actuators 320, for example motors, via a second wire harness for example. The collar 305 may rotate and send its rotational information to the control board 315 via a third wire harness for example. The electromechanical actuators 320, are contained within a proximal enclosure 325. The proximal enclosure 325, attaches to the distal enclosure 330. In some embodiments, the collar 305, may facilitate the connection between the proximal enclosure 325 and the distal enclosure 330. The distal enclosure 330 rotatably attaches to a catheter support cowling 335. The catheter support cowling 335 is gearably coupled to a transmission assembly 340. The transmission assembly is gearably coupled to the electromechanical actuators 320. The electromechanical actuators 320 provide the mechanical actuation forces to rotate the catheter support cowling 335. In the depicted figure, the catheter support cowling 335 is releasably attached to a catheter 345. The CMH's releasable attachment of the catheter may advantageously provide the ability to detach and dispose of the catheter 345, and may provide re-use of the CMH. When coupled to the catheter support cowling 335, the catheter 345 is rotated by the catheter support cowling 335, which may advantageously provide additional catheter steering flexibility, since the user may not only deflect the catheter tip in the direction of catheter advancement, but may optionally rotate a pre-bent catheter tip in that direction as well. The motor-assisted rotation of the support cowling 335, which rotates the catheter 345, substantially reduces the need for user-assisted manual handle rotation.

In some embodiments, the capacitive touch wheel 310 may be part of a user input and visual feedback feature that may take the form of a small touchscreen display. The touchscreen display may advantageously provide an adaptable method of feeding back information, for example biological measurements to the user. In such embodiments, the small touchscreen display may advantageously change from showing catheter measurements, for example catheter tip temperature, to user input selections, such as steering arrow buttons, for example. Embodiments of a display device coupled to the CMH are described in further detail with reference to FIG. 6.

In some embodiments, the user feedback may take the form of visual indicators such as LEDs. The LEDs may advantageously provide the user with visual feedback that may be noticed by the user's peripheral vision, for example a warning LED for catheter forces within the range of impending tissue perforation.

In some embodiments, the user input may take the form of conventional buttons. The conventional buttons may advantageously provide use behind substantially translucent sterile barriers. The user may benefit from a tactile feel of a button under such barriers.

In some embodiments, the user may be in direct contact with the CMH, holding the CMH in their hand. The forces on the catheter from the catheter tip hitting a vessel wall, for example, may be felt by the user, which may advantageously provide a natural haptic feedback. This haptic feedback may be amplified or augmented by the CMH. In some embodiments, haptic feedback may be artificially induced into the proximal enclosure 325, for instance with a vibrator module. In some embodiments, the vibrational induction may be made by the existing electromechanical actuators 320, which may advantageously repurpose the actuators to produce a vibration, for example in short bursts.

In some embodiments, the level of haptic experience may be predetermined for each user, which may advantageously provide suitable haptic sensations with amplification or gain customized and scaled to each user of the CMH. One or more user profiles may contain user preference or default amplification value configurations for various feedback signals. In some implementations, profile amplification configurations may be stored in a non-volatile memory space accessible by a processor in the CMH. During CMH operation, a surgeon, for example, may make inputs via the user interface to select a desired feedback amplification configuration suitable for a particular surgical procedure. During a surgical procedure, as an illustrative example, one or more haptic feedback amplification configurations may be employed by retrieving corresponding stored amplification settings from the non-volatile memory. The profile or configuration settings employed at any point during the surgical procedure may be, for example, dynamically selected as a function of the type of surgical procedure, the determined chamber volume in which the distal tip is located, proximity to certain sensitive tissues, or a combination such factors.

In some embodiments, the catheter may provide the user feedback that a body cavity wall has been touched. In some examples the sensor providing the touch sense may be a contact sensor, which may advantageously provide high precision. In an illustrative example, during cardiac ablations, the touch sensors may provide precise contact force and direction information, which may advantageously provide data for cardiac mapping.

In some embodiments, the sensor may be a capacitive touch sensor, which may advantageously provide high sensitivity. The high sensitivity provides medical teams with more useful and detailed data to aid in the diagnosis of medical conditions. In some examples the capacitive sensor may quantify a subjective sense of touch.

In some embodiments, the sensor may be a pressure sensor, which may advantageously provide substantial immunity to non-wall tissues and fluids.

In some embodiments, the sensor may be a force sensor, which may advantageously provide substantial immunity to non-wall tissues and fluids and may provide bending force information.

In some embodiments, the sensor may be ultrasonic, which may advantageously provide proximity information.

In some embodiments, the sensor may be part of the electromechanical actuator, where the electrical current may be monitored to determine how much work is being done on the control wires, by a control system operating to maintain a commanded deflection angle of the catheter tip, allowing the CMH to warn the user to stop, for example.

In some embodiments, a force sensor may be provided on the control wires, which may advantageously provide feedback to the user when the current bend command may not be possible in the current catheter tip position.

In some embodiments, the catheter tip may contain a combination of one or more different types of sensors and/or different types of instruments that cooperate to measure one or more biological functions, or to execute one or more medical procedures. In these embodiments, the signals to and from the sensors and instruments may route through the CMH.

In some embodiments, the electromechanical actuators 320 may provide the tension to the control wires as explained in FIG. 1 detail A. In some embodiments, the electromechanical actuators 320 may be a stepper motor which may advantageously provide substantially precise angular control of the motor and therefore the tension to the control wires. In some embodiments, the electromechanical actuators 320 may be a servo, a conventional motor coupled to a sensor for position feedback, which may advantageously provide a simplified design for firmware. In some embodiments, electromechanical actuators 320 may be used to create rotational motion, which can be converted to a linear motion necessary for control wire actuation via a transmission mechanisms, for example, a winch mechanism, where multiple rotations of an axle to take in or let out wire, which may advantageously provide additional torque, a rocking cam wheel, where partial rotations to take in or let out wire, which may advantageously provide increased resolution of the catheter deflection, a reel mechanism with a stationary axle with a traveling shuttle to wrap the wire, which may advantageously avoid control wire entanglement, a "feeder" wheel where tension is applied by friction on the control wires running between two rolling wheels, which may advantageously provide an easier maintainable device, or a cogged actuation where chain or a toothed belt interface to a gear, advantageously avoiding slippage.

In some embodiments, the electromechanical actuators 320 may employ for example, solenoids or other electromagnetic forces to induce linear motion, advantageously applying a direct push or pull.

In some embodiments, solenoid-type actuations may be imitated with hydraulic or pneumatic systems. In some embodiments, direct deformation of the catheter shaft may be achieved via targeted thermal expansion or contraction or forces stemming from the piezoelectric effect upon application of voltage.

In some embodiments, additional methods for adjusting control wires may be utilized without robotic (motorized) augmentation.

Figure 4:
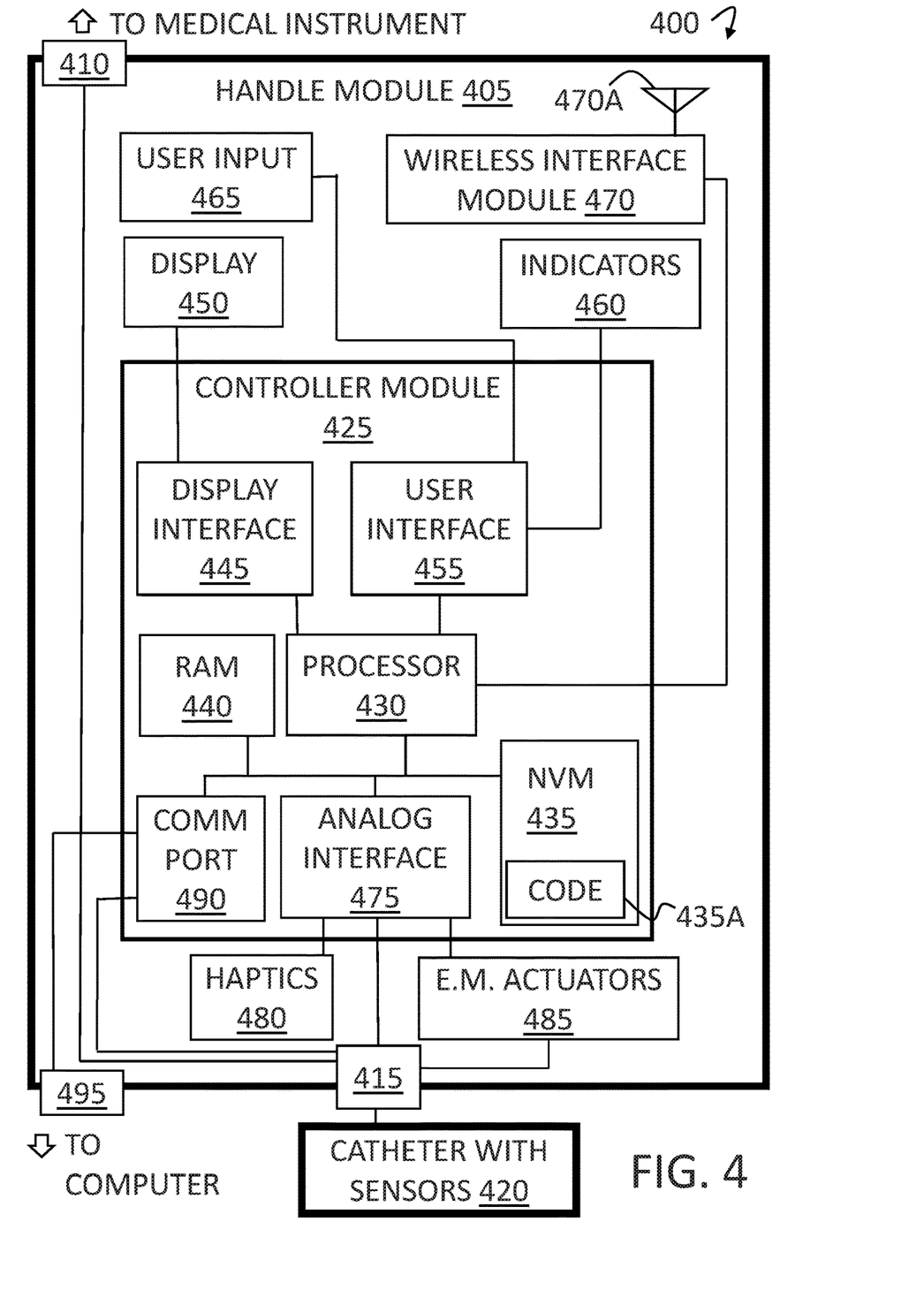
FIG. 4 depicts a schematic view of an exemplary CMH functional block diagram.

FIG. 4 depicts a schematic view of an exemplary CMH functional block diagram. The system 400 includes a handle module 405. The handle module 405 electrically connects to a medical instrument, for example an instrument that treats uncontrolled hypertension through renal nerve denervation via a catheter-based medical procedure, via a medical instrument port 410. The medical instrument port 410 passes the medical instrument signals to the catheter port 415. The catheter port 415 connects to the detachable and disposable catheter with sensors 420.

The handle module 405 also includes the controller module 425. In some embodiments, the controller module 425 may represent the control board as depicted in FIG. 3, item 315. The controller module 425 includes a processor 430 that acts as the main processing and control component for the controller module 425.

The processor 430 connects to Non-Volatile Memory (NVM) 435 where the executable code 435A is programmed and contained. To facilitate the processor 430 functionality, connection to Random Access Memory (RAM) 440 is provided. The processor 430, NVM 435, and RAM 440 build the basic digital control platform. In some embodiments, the CMH may save steps and catheter moves into the NVM 435, advantageously allowing a user to read from NVM 435 particularly difficult or lengthy catheter move sequences from CMH memory. In some embodiments, an entire sequence of catheter moves made for a specific patient may be saved to NVM 435, so that a user may read from NVM 435 and replay those predetermined moves (deflections and/or rotations) for another catheter located in the same or nearby lumen. In some embodiments, the CMH may be preprogrammed to execute the exact number of catheter rotations required for a procedure, for example. In some embodiments, a map of rotational angles may be saved in the CMH memory, so that the user may employ the predetermined sequence at a predetermined point in the medical procedure.

The processor 430 communicates to a display interface 445. The display interface 445 then drives the display 450. In some embodiments, the display may be a capacitive touch wheel, that displays the functions of the capacitive touch wheel. In some embodiments, the display may be large enough to display graphs of biological signals, which may advantageously provide additional patient statistics to the user. In some embodiments, the display may provide catheter mapping to guide the user in catheter steering procedure. In some embodiments, the display may provide instructions, which may advantageously provide 'just in time' training. In some embodiments, the CMH may provide the user, via the user interface, a prompt when the user is to make the next catheter move, which may advantageously provide catheter guide assistance to the user.

The processor 430 also communicates to a user interface 455. The user interface 455 then drives various indicators 460. The user interface 455 is also responsible for reading the various user input 465, push buttons for example.

The processor 430 also communicates to wireless interface module 470. The wireless interface module 470 includes an antenna 470A. The wireless interface module 470 may provide wireless communication to a computer or other medical instrument, for example.

The processor 430 also communicates to an analog interface 475. The analog interface 475 is responsible for driving the haptic devices 480. The analog interface 475 is also responsible for receiving and conditioning the signals from the catheter port 415 which is connected to the catheter and sensors 420. Finally, the analog interface 475 contains the drive circuitry to drive the electromechanical actuators 485.

The processor 430 also communicates to a communication port 490. The communication port 490 is connected to the communication port interface connector 495. The communication port interface connector 495, advantageously provides digital communication to the CMH, to enable user programming of the CMH from a computer for example. In some embodiments, the CMH may be programmed, by a computer connection, with an app, to perform certain surgeries, for example therapeutic or diagnostic.

The handle module 405 may contain the electronics and mechanical components that provide user interface controls to motor-assist and to mechanically augment a user's direct maneuvering of a guide catheter, and to provide haptic feedback to the user.

Figure 5A:
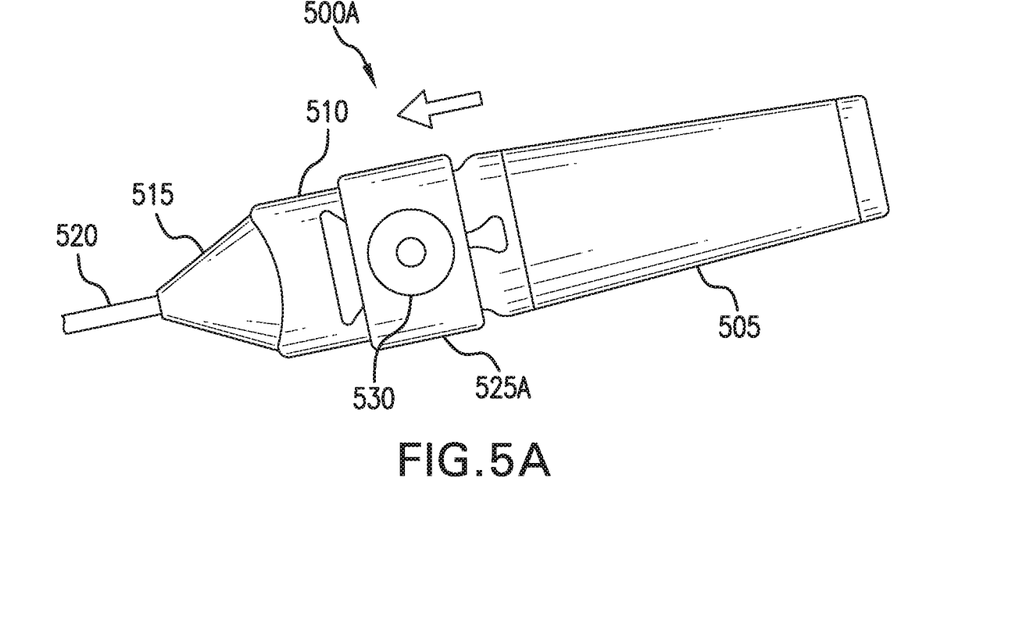
FIG. 5A depicts a perspective view of an exemplary CMH, illustrating a locking collar embodiment in an unlocked state.

FIG. 5A depicts a perspective view of an exemplary CMH, illustrating a locking collar embodiment in an unlocked state. The unlocked collar CMH embodiment 500A, includes a handle proximal end 505. The handle proximal end 505 rotatably couples to the handle distal end 510. The handle distal end 510 rigidly couples to a catheter support cowling 515. The catheter support cowling 515 is releasably coupled to a catheter 520. The handle distal end 510 and the handle proximal end 505 are further slidably coupled to a locking collar 525A. The locking collar 525A is depicted in the slid forward position, exemplifying an unlocked position. In this position the user may freely rotate the locking collar 525A. The locking collar 525A contains a user interface 530. In some embodiments, the user interface 530 may be a capacitive touch wheel, which may advantageously provide control of the CMH with finger sliding motions, and provide a modern look. The handle distal end 510 rigidly coupled to a catheter support cowling 515, may advantageously allow the user to manually rotate the handle distal end 510 and the catheter 520 around the longitudinal axis. In some embodiments, the handle distal end 510 may be rotatably coupled to the catheter support cowling 515, and advantageously allows the user to employ powered rotation of the catheter 520 around the longitudinal axis.

Figure 5B:
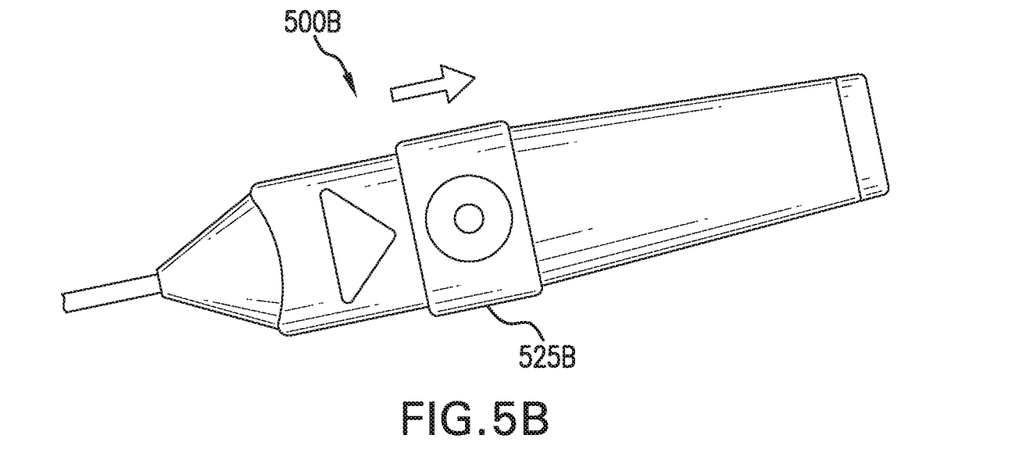
FIG. 5B depicts a perspective view of an exemplary CMH, illustrating a locking collar embodiment in a locked state.

FIG. 5B depicts a perspective view of an exemplary CMH, illustrating a locking collar embodiment in a locked state. The locked collar CMH embodiment 500B further depicts the collar 525B in a slid back position, exemplifying a locked position. In this position, the user may rotate the locked collar embodiment to rotate the catheter 520.

In some embodiments, the locking collar 525A may function in the reverse direction. In such embodiments, the collar may slide toward the handle proximal end 505 to allow free rotation of the handle proximal end 505. The collar may then slide toward the handle distal end 510, to relock the handle from rotation.

In some embodiments, the handle distal end 510 and the handle proximal end 505 may be rigidly coupled, such that the collar may enter and exit free rotation by the lock and unlock action. In some embodiments, the handle distal end 510 and the handle proximal end 505 may be unitary, which may advantageously reduce bill of materials parts count.

In some embodiments, the user interface 530 containing buttons, indicators and displays, for example, may be on the handle proximal end 505, such that rotation of the handle proximal end 505 may allow reorientation of the controls toward the user.

In some embodiments, the locked position may provide control over an axis of powered motion. In some examples a collar may employ an isometric sensor such that the user may apply rotational force to the collar in either direction to control the catheter tip deflection. In some examples, the collar may employ a toggle switch, such that the user may rotate the collar in either direction to control the catheter tip deflection. In some embodiments, the user interface 530 may control one axis of tip deflection, for example forward and backward, and the collar may control a different axis of tip deflection, for example left and right.

In some embodiments, the CMH may allow the internal components to rotate. In these embodiments, the electromechanical actuators may be on a bearing independent of the CMH enclosure. In these embodiments, the handle may remain flat and substantially unmoving, while the user may reposition the rotational position of the user interface, advantageously allowing the user to orient the user interface independent of the rest of the CMH, and allowing the user to drive the CMH with one hand. The locking collar 525A may decouple from the rest of the CMH to reorient the catheter tip.

In an illustrative implementation, a user may push the locking collar 525B forward and advance the catheter 520 until the catheter tip has reached a predetermined target destination in the patient. The user may then snap the locking collar 525B back into place, and manipulate the CMH with one hand by using a thumb to drive the catheter tip in one axis and an index finger to drive the catheter tip in the other axis, for example.

In some embodiments, the user interface 530 may use a capacitive touch sensor to receive user input. The capacitive touch sensor may be located in more than one position on the CMH, which may advantageously provide the user the ability to control the CMH with more than one finger or thumb. The user interface may be a single-axis strip, which may advantageously provide isolated control of each catheter axis. The capacitive touch sensors may be a ring, which may advantageously provide an intuitive control motion, and may advantageously provide control with a single finger. The capacitive touch sensors may be a two-dimensional trackpad as employed on laptop computers, which may advantageously provide unencumbered use under a sterile barrier. The capacitive touch sensors may be contoured which may advantageously provide optimized ergonomics. The capacitive touch sensors' inputs may provide position-based or velocity-based response in the catheter tip. In some embodiments, the input force to the capacitive touch sensors may advantageously control tip response sensitivity or speed of the tip's angular deflection and/or rotation.

In some embodiments, the user interface 530 may employ other types of user interface components, such as momentary switches, for example. Momentary switches may advantageously provide tactile feedback to the user. Resistive switches may be employed on the user interface components to facilitate button actuation with a gloved hand.

In some embodiments, the CMH 500A may employ concentric collars around the device, transducing rotation of the collar relative to the device. In some embodiments, the user interface 530 may employ a joystick, which may advantageously provide user-intuitive controlling motion. In some embodiments, the user interface 530 may employ a linear slider, which may advantageously provide decoupled axis control. In some embodiments, the user interface 530 may employ a wheel rotating on an axis, which may advantageously provide fast movement. In some embodiments, the user interface 530 may employ a plane tilting on a central point, similar to a joystick, which may advantageously provide control through a sterile barrier without encumbrance. In some embodiments, the user interface 530 may employ a stationary "roller ball", which may advantageously provide transducing inputs from rotation around two axes. In some embodiments, the user interface 530 may employ a graphical touch screen, providing dynamic interface, advantageously repurposing the user interface functionality to provide only the inputs needed at the programmed time. In some embodiments, the user interface 530 may employ a remote wireless device with any of the listed control inputs, advantageously speeding setup and reducing the number of cables. In some embodiments, the user interface 530 may employ direct translation, where the user directly manipulates a physical model of the catheter tip to model the desired catheter tip movement, and the system responds by sensing the model's position based on flex sensors within the model or on machine vision processing performed on images from an external camera focused on the model.

In some embodiments, the user interface 530 may combine multiple modes of input, for example a capacitive touch sensor on a concentric collar or linear slider. In some embodiments, the user interface 530 may provide control over a single axis at a time, or over multiple axes simultaneously.

Figure 6:
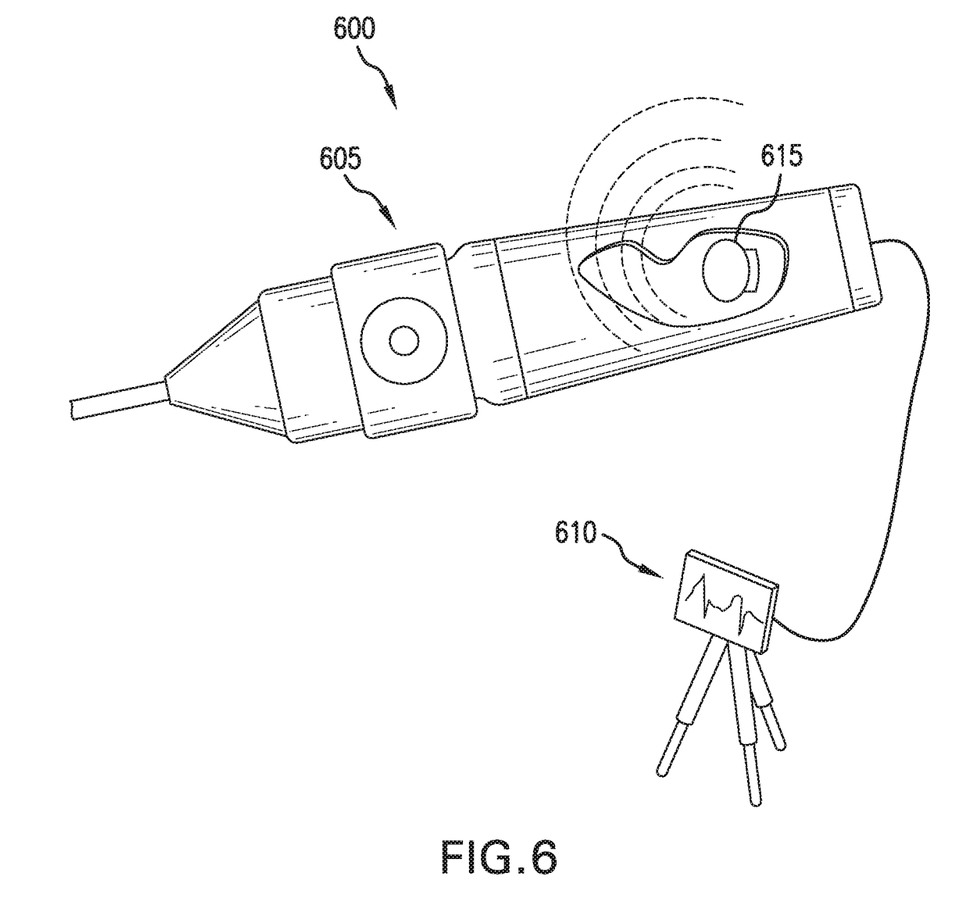
FIG. 6 depicts a perspective view of an exemplary CMH with a remote display and audible feedback.

FIG. 6 depicts a perspective view of an exemplary CMH with a remote display and audible feedback. A CMH system 600, includes a CMH 605 connected to a remote display 610. In some embodiments, the remote display may include flexible twistable legs, such that the remote display 610 may be mounted to other operating room equipment, for example. The CMH 605 includes an audio transducer 615. In some embodiments, the user may benefit from an audible alert, in an environment that contains visual distractions, for example.

Figure 7A:
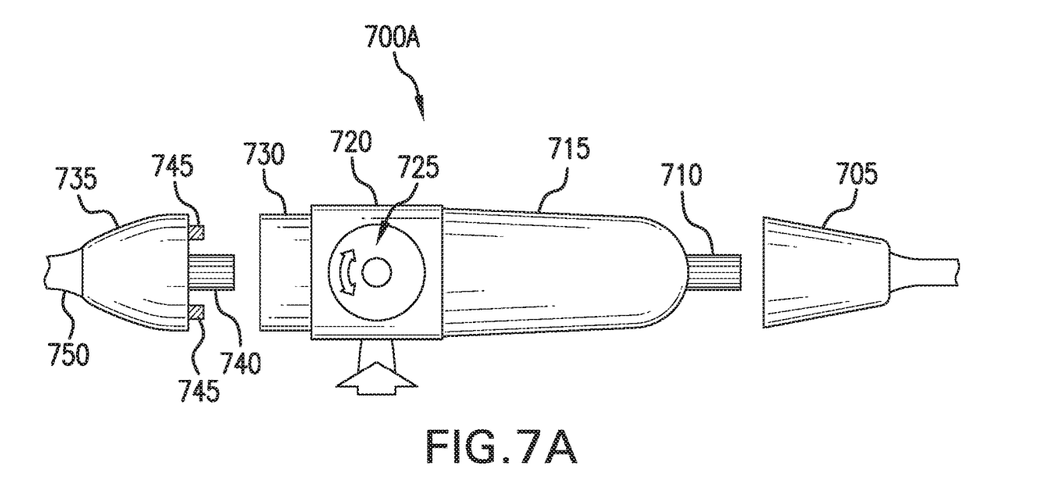
FIG. 7A depicts a perspective view of an exemplary CMH, illustrating a user interface with rotating concentric collar, carrying a circular "scroll wheel" sensor.

FIG. 7A depicts a perspective view of an exemplary CMH, illustrating a user interface with rotating concentric collar, carrying a circular "scroll wheel" sensor. A CMH 700A, is attached to an instrument, for example an ultrasound generator, via an instrument cord 705. The instrument cord is releasably and electrically connected to an instrument plug 710. The instrument plug 710 is included in a handle 715. The handle 715 is rotatably attached to a rotating concentric collar 720. The rotating concentric collar 720 is fixedly attached to a circular "scroll wheel" sensor 725. The rotating concentric collar 720 is rotatably attached to a body 730. The body 730 is releasably connected to a replaceable catheter head 735. The replaceable catheter head 735 includes an electrical catheter plug 740. The replaceable catheter head 735 also includes 2 control wire plugs 745. The replaceable catheter head 735 is rigidly coupled to the catheter shaft 750.

Figure 7B:
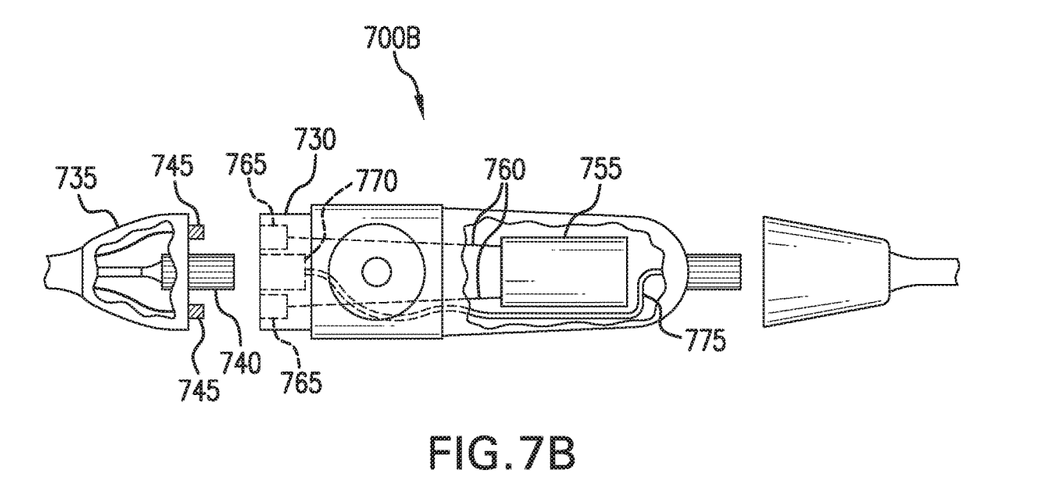
FIG. 7B depicts a perspective view of an exemplary CMH, illustrating a releasable mechanical and electrical interface.

FIG. 7B depicts a perspective view of an exemplary CMH, illustrating a releasable mechanical and electrical interface. A CMH 700B, includes an electromechanical actuator 755. The electromechanical actuator is fixedly attached to the pair of control wires 760. The control wires 760 route to the body 730 where the control wires 760 attach to a pair of control wire jacks 765. The control wire jacks 765 removably attach to the control wire plugs 745. The control wire plugs 745 are fixedly attached to the replaceable catheter head 735. The replaceable catheter head 735 includes the electrical catheter plug 740. The electrical catheter plug 740, removably attaches to an electrical catheter jack 770. The electrical catheter jack 770 electrically connects to a handle pass-through harness 775. The handle pass-through harness 775 connects to the instrument plug 710. In some embodiments, a second electrical interface is employed to route data to external equipment. A catheter coupling consisting of 1) the mating pair of the electrical catheter plug 740, and the electrical catheter jack 770 and 2) the mating pair of the control wire plugs 745, and the control wire jacks 765, transmit the electronic signal from the replaceable catheter head 735 to the CMH 700B.

In some embodiments, the catheter coupling may allow the user to separate the CMH 700B from replaceable catheter head 735. The catheter coupling will provide a robust connection between the control wire plugs 745, and the control wire jacks 765.

The catheter coupling will also provide a reliable electrical connection between the electrical catheter plug 740, and to the electrical catheter jack 770, for example the electrical signals from an ultrasound transducer.

In some embodiments, the replaceable catheter head 735 may be latched onto the body 730 with internal or external clips, which may advantageously provide quick attachment. In some embodiments, the replaceable catheter head 735 may be screwed onto the body 730 with multi-turn standard thread screws, which may advantageously provide a secure connection with a tool. In some embodiments, the replaceable catheter head 735 may be latched onto the body 730 with or a 'Luer Lock' type screw, which may advantageously provide a partial turn connection that is both secure and quick. Screw-type embodiments may involve the replaceable catheter head 735 threading onto the body 730. In some embodiments, the application of discrete screws through clearance holes and into threaded receiving holes may be employed.

In some embodiments, the catheter coupling may include rigid ends on the control wires 760, which may be captured within the replaceable catheter head 735 by conformed (mating) receptacles. This may be achieved with the rotation of the replaceable catheter head 735 relative of the body 730, advantageously locking the replaceable catheter head 735 into place. In some embodiments, the control wires 760 may be captured by inserting barbed ends of the control wires 760 into replaceable plastic or hard rubber inserts on the body 730, or by implementing spring-action barbs such as employed, in small scale, on electrical crimp-connectors inserted into plastic housings. In some embodiments, bare control wire 760 ends may be guided directly through a friction-feed actuator.

In some embodiments, the catheter coupling may include magnets to direct force or to assist in guiding mating parts to their receptacle inside the CMH 700B. In some embodiments, the catheter coupling may include screws mating to the control wires 760. In some embodiments, the catheter coupling may include screws perpendicular to the control wires 760 to clamp the control wires 760 to the electromechanical actuator or to pass through a coupling hole. In some embodiments, the catheter coupling may include a cylindrical, or helically wound braid to capture inserted parts, which may advantageously provide fast assembly. In some embodiments, the catheter coupling may include a cam lock as employed on pipe connections. In some embodiments, the catheter coupling may include a spring lock as employed on many in-line couplings, for example an external spring ring as employed on tractor hitches. In some embodiments, the catheter coupling may include an internally sprung ball bearing, as employed on bit driver handles. In some embodiments, the catheter coupling may include a hook-shaped end passing through a hole to capture the mating piece.

In some embodiments, rotational motion may be transferred to the replaceable catheter head 735, directly via gears, pulleys, or splined shafts, wherein the replaceable catheter head 735 may convert rotational motion into the linear motion on the control wires 760.

In some embodiments, a tilting mechanism in the body 730 may couple to a receiving tilting mechanism within the replaceable catheter head 735. In some embodiments, the mechanism may consist of a single multi-axis gimbal, providing a simplified operation. In some embodiments, multiple single-axis pivots may be employed, which may advantageously provide flexibility in many directions. In some embodiments, the replaceable catheter head's 735 receiving tilting mechanism may be coupled directly to the control wires 760.

In some embodiments, the replaceable catheter head 735 and the body 730 may be permanently connected.

Although various embodiments have been described with reference to the mechanical catheter coupling, other embodiments are possible. For example, some catheters may be rigidly coupled to a distal portion of the CMH, and the distal portion of the catheter may be driven to rotate by a motor drive in the CMH. In some examples, a motor drive (e.g., stepper motor) may directly drive the distal portion, which in turn rotates the catheter about the longitudinal axis of the CMH. In some implementations, a gear system may couple the motor to the distal portion, such that a higher speed motor operation may impart a higher torque, slower rotation to the catheter.

In some embodiments, the catheter coupling may transmit data and power to and from a catheter tip transducer. In some embodiments, the catheter electrical connection may be high speed and high bandwidth to allow transmission of many channels of data and may provide power to operate an installed sensor. In some embodiments, the catheter coupling may implement high-density rectangular connectors consisting of two mating ends: male pins and female receptacles. In some embodiments, the catheter coupling may implement optoelectronic connections that transduce electricity to and from packets of photons, including a possible transduction to optical signals within the transducer.

In some embodiments, the catheter coupling may implement spring pin contacts that interface by pressing onto receiving pads.

In some embodiments, the catheter coupling may implement printed circuit board edge connectors.

In some embodiments, the electrical signals in the handle pass-through harness 775 may pass the electrical catheter interface around the body 730 through a wire bundle, for example, that may be connected with either a standard rigid connection or a rotating interface to avoid wrapping the wire as the replaceable catheter head 735 and body 730 are manipulated.

Although various embodiments have been described with reference to the figures, other embodiments are possible. For example, some embodiments may allow manual over-ride control of the CMH, advantageously giving the user a fallback operating mode while the CMH continues to provide haptic feedback.

Various embodiments may employ user interface elements for generating a rotation command signal in response to user input. A catheter rotatably coupled to a CMH may rotate about a longitudinal axis in response to rotation of a motor drive that is in turn rotated in response to a rotational command signal. With reference to the figures described above, examples of user interface elements capable of generating a rotation command signal may include, but are not necessarily limited to, items referred to as 115, 120, 310, 465, 530, 525A, 525B, 725, and 720.

In some embodiments, the user input signals may be conditioned according to user preference. Some embodiments may allow custom mapping of a 'transducer axis to catheter tip axis' or tuning 'actuator sensitivity to transducer input'. The system may also track session data to process with learning tools and/or incorporating learning algorithms for users to analyze their performance. This allows the use of the tracked data for training purposes and optimization of user performance. Settings and tracked data may be accessible via internal or external software applications.

In some embodiments, the CMH will include a "smart" interface capable of customization that provides data tracking for training and other purposes. The "smart" interface may provide computer access to transfer data to and from the CMH. The "smart" interface may interface to an external computer running a software application, and may contain a dashboard to manage the data collection and device configuration. The "smart" interface may allow the user to set the user interface controls to a predetermined functionality and may allow the user to set the catheter control sensitivity to a predetermined level.

Some embodiments may be disposable, advantageously eliminating the cost of sterilization. Some embodiments may be non-disposable, advantageously saving the cost to hospitals and ultimately to the patient, of purchasing a new CMH for every procedure.

Some embodiments may determine the cavity space that the catheter is within. In these embodiments, the CMH may reduce the movement allowance the user may execute, thereby re-calibrating the movement resolution. In some examples the cavity sense may be accomplished using a proximity sensor. In some examples the cavity sense may be accomplished using an infrared sensor. In some examples the cavity sense may be accomplished using an ultrasonic sensor. In some examples the cavity sense may be accomplished using sound. In some examples the cavity sense may be accomplished using optical means, for example camera imaging. In various examples, the cavity sense may employ 'deep learning' and pattern recognition in a wide variety of signals. By way of example and not limitation, optical signals may be processed to recognize patterns.

In some examples the gain of the haptic feedback may be based on the detected volume of the chamber and may allow the CMH to employ a 'predetermined sensitivity rating' which may be automatically set, in response to the sensitivity of the area that the catheter is in or in response to the distance of the catheter advancement. In some embodiments, the automatic sensitivity setting may be a function of the catheter tip force, the size of the chamber, or the chamber volume. In some embodiments, the CMH may receive parameters that affect sensitivity sensing, such as chamber size, or chamber volume, from internal or external systems, including those that are provided to the user as part of the CMH or products from third-party suppliers.

In some embodiments, the electromechanical actuator may reach a torque limit and provide a clicking sound and feel that may be haptic feedback to the user.

In some embodiments, the rotatable collar may exist in more than one location on the CMH. In some embodiments, the user interface may exist in more than one location on the CMH.

In an illustrative example, a surgeon may manipulate a guide catheter through a patient's femoral artery using the CMH. In various examples, a surgeon employs the user interface (UI) on the CMH to control electromechanical actuators within the CMH to pull on control wires within a guide catheter to deflect the catheter tip and thereby steer the guide catheter to its destination, for example, to capture echocardiogram images in a patient's heart. The CMH may provide augmented mechanical control with haptic feedback to the user when performing direct (e.g., not in a remote cockpit) guide catheter based procedures.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the first receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), wireless and/or optical networks, and the computers and networks forming the Internet. Other implementations may transport messages by broadcasting to all or substantially all devices that are coupled together by a communication network, for example, by using Omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Fire wire, ATA/IDE, RS-232, RS-422, RS-485, 802.11 a/b/g, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In some embodiments, the CMH may be a handheld robotically augmented catheter steering handle, the augmentation may advantageously provide vision, precision and feedback to the user.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A hand-held catheter apparatus, comprising:
   a handle body extending from a proximal end to a distal end along a longitudinal axis;
   an interface module coupled to the handle body, wherein the interface module is configured to generate a rotation command signal in response to a remotely generated control signal;
   a rotational actuator module positioned in the handle body and having a rotatable output, wherein the rotational actuator module controls an angular rotation of the rotatable output in response to the rotational command signal;
   a handle coupling disposed at the distal end of the handle body and configured to releasably couple to a replaceable catheter head at a proximal end of a disposable catheter structure adapted to extend distally therefrom, wherein when the handle coupling is engaged with the catheter head, the rotational actuator module is operative to rotate the catheter structure about the longitudinal axis in response to rotation of the rotatable output, wherein the handle coupling comprises a handle deflection interface adapted to releasably couple to a catheter deflection interface in the catheter head;
   a first deflection actuator disposed in the handle body and configured to impart, via the handle deflection interface and the catheter deflection interface, a first deflection angle command in a first plane to a steerable tip at a distal end of the catheter structure.

2. The apparatus of claim 1, wherein the interface module comprises a wireless antenna configured to receive the remotely generated control signal.

3. The apparatus of claim 1, wherein the remotely generated control signal is received by the interface module via a fiber optic link.

4. The apparatus of claim 1, wherein the interface module is configured to receive the remotely generated control signal from a computer.

5. The apparatus of claim 1, wherein the interface module is configured to receive the remotely generated control signal from a medical instrument.

6. The apparatus of claim 5, wherein the remotely generated control signal comprises medical instrument signals.

7. The apparatus of claim 1, further comprising:
   a processor positioned in the handle body;
   a non-volatile memory coupled to the processor and containing a program of instructions that, when executed by the processor, cause the processor to perform operations to execute predetermined catheter moves required for a corresponding procedure.

8. The apparatus of claim 7, further comprising:
   an analog interface module electrically coupled to the processor, wherein the analog interface module is configured to receive and condition signals from the handle coupling and to drive the rotational actuator.

9. The apparatus of claim 8, further comprising:
   a display on an outer surface of the handle body and configured to display graphs of biological signals; and,
   a display interface coupled to the processor configured to drive the display.

10. The apparatus of claim 9, wherein the display comprises a capacitive touch wheel.

11. The apparatus of claim 10, further comprising:
    a collar attached to the capacitive touch wheel, wherein the collar is configured to rotate and send its rotation information to the processor.

12. The apparatus of claim 11, wherein the collar comprises a locking collar.

13. The apparatus of claim 11, further comprising:
    a user interface electrically coupled to the processor, wherein the user interface is configured to drive a plurality of indicators; and,
    user inputs, and the user interface is further configured to read signals via the user inputs.

14. The apparatus of claim 13, wherein the user inputs comprise push buttons.

15. A hand-held catheter apparatus, comprising:
    a handle body extending from a proximal end to a distal end along a longitudinal axis;
    an interface module coupled to the handle body, wherein the interface module is configured to generate a rotation command signal in response to a remotely generated control signal, wherein the remotely generated control signal is received by the interface module via a wireless link;
    a rotational actuator module positioned in the handle body and having a rotatable output, wherein the rotational actuator module controls an angular rotation of the rotatable output in response to the rotational command signal;
    a handle coupling disposed at the distal end of the handle body and configured to releasably couple to a replaceable catheter head at a proximal end of a disposable catheter structure adapted to extend distally therefrom, wherein when the handle coupling is engaged with the catheter head, the rotational actuator module is operative to rotate the catheter structure about the longitudinal axis in response to rotation of the rotatable output, wherein the handle coupling comprises a handle deflection interface adapted to releasably couple to a catheter deflection interface in the catheter head;
    a first deflection actuator disposed in the handle body and configured to impart, via the handle deflection interface and the catheter deflection interface, a first deflection angle command in a first plane to a steerable tip at a distal end of the catheter structure.

16. The apparatus of claim 15, wherein the interface module comprises a wireless antenna configured to receive the remotely generated control signal.

17. The apparatus of claim 15, wherein the interface module is configured to receive the remotely generated control signal from a computer.

18. The apparatus of claim 15, wherein the interface module is configured to receive the remotely generated control signal from a medical instrument.

19. The apparatus of claim 18, wherein the remotely generated control signal comprises medical instrument signals.

20. The apparatus of claim 15, further comprising:
   a processor positioned in the handle body;
   a non-volatile memory coupled to the processor and containing a program of instructions that, when executed by the processor, cause the processor to perform operations to execute predetermined catheter moves required for a corresponding procedure;
   user inputs, and the user interface is further configured to read signals via the user inputs.

\* \* \* \* \*